United States Patent [19]
Chu et al.

[11] Patent Number: 5,817,667
[45] Date of Patent: Oct. 6, 1998

[54] COMPOUNDS AND METHODS FOR THE TREATMENT OF CANCER

[75] Inventors: Chung K. Chu, Athens, Ga.; Yung-Chi Cheng, Woodbridge, Conn.

[73] Assignees: University of Georgia Research Foudation, Athens, Ga.; Yale University, New Haven, Conn.

[21] Appl. No.: 301,298

[22] Filed: Sep. 6, 1994

Related U.S. Application Data

[63] Continuation-in-part of Ser. No. 937,845, filed as PCT/US92/03144 Apr. 16, 1992.

[51] Int. Cl.⁶ .................. A61K 31/505; A61K 31/675
[52] U.S. Cl. .................................... 514/274; 514/86
[58] Field of Search .................. 544/310; 514/252, 514/232, 274, 86

[56] References Cited

U.S. PATENT DOCUMENTS

| | | |
|---|---|---|
| 4,000,137 | 12/1976 | Dvonoch et al. . |
| 4,336,381 | 6/1982 | Nagata et al. . |
| 4,861,759 | 8/1989 | Mitsuya et al. . |
| 4,879,277 | 11/1989 | Mitsuya et al. . |
| 4,900,828 | 2/1990 | Belica et al. . |
| 4,916,122 | 4/1990 | Chu et al. . |
| 4,963,533 | 10/1990 | de Cleroq et al. . |
| 4,968,674 | 11/1990 | Taniyama et al. . |
| 5,041,449 | 8/1991 | Belleau et al. ................... 514/274 |
| 5,047,407 | 9/1991 | Belleau et al. . |
| 5,059,690 | 10/1991 | Zahler et al. . |
| 5,071,983 | 12/1991 | Koszalka et al. . |
| 5,151,426 | 9/1992 | Belleau et al. . |
| 5,179,104 | 1/1993 | Chu et al. . |
| 5,185,437 | 2/1993 | Koszalka et al. . |
| 5,204,466 | 4/1993 | Liotta et al. . |
| 5,210,085 | 5/1993 | Liotta et al. . |
| 5,234,913 | 8/1993 | Furman, Jr. et al. . |
| 5,248,776 | 9/1993 | Chu et al. . |
| 5,270,315 | 12/1993 | Belleau et al. . |
| 5,444,063 | 8/1995 | Schinazi . |
| 5,466,806 | 11/1995 | Belleau et al. . |

FOREIGN PATENT DOCUMENTS

| | | |
|---|---|---|
| 0 206 497 | 12/1986 | European Pat. Off. . |
| 0 217 580 | 4/1987 | European Pat. Off. . |
| 337713 | 10/1989 | European Pat. Off. . |
| 0 352 248 | 1/1990 | European Pat. Off. . |
| 0 375 329 | 6/1990 | European Pat. Off. . |
| 3825526 | 8/1990 | European Pat. Off. . |
| 0 433 898 | 12/1990 | European Pat. Off. . |
| 0 494 119 | 7/1992 | European Pat. Off. . |
| 0 515 144 | 11/1992 | European Pat. Off. . |
| 0 515 156 | 11/1992 | European Pat. Off. . |
| 0 515 157 | 11/1992 | European Pat. Off. . |
| 0 526 253 | 2/1993 | European Pat. Off. . |
| WO 92/10496 | 6/1992 | Japan . |
| WO 88/07532 | 10/1988 | WIPO . |
| WO 90/12023 | 10/1990 | WIPO . |
| WO 91/11186 | 8/1991 | WIPO . |
| WO 91/17159 | 11/1991 | WIPO . |
| WO 92/10497 | 6/1992 | WIPO . |
| WO 92/14729 | 9/1992 | WIPO . |
| WO 92/14743 | 9/1992 | WIPO . |
| WO 92/15308 | 9/1992 | WIPO . |
| WO 92/18517 | 10/1992 | WIPO . |
| WO 92/21676 | 10/1992 | WIPO . |
| WO 94/14456 | 7/1994 | WIPO . |
| WO 94/27616 | 12/1994 | WIPO . |
| WO 95/18137 | 7/1995 | WIPO . |
| WO 95/20595 | 8/1995 | WIPO . |
| WO 95/21183 | 8/1995 | WIPO . |

OTHER PUBLICATIONS

Ball, C. R., et al., Transplantable Colon Tumers as Chemotherapy Screening Models, *Cancer(phila.)* 36:2437–2440 (1975).

Balzarini, J. et al., "Potent and Selective Anti–HTLV–III/LAV Activity of 2',3'–Dideoxycytidinene, . . . ," *Bioch. and Bioph. Res. Comm.* 140(2):735–742 (1986).

Beach, J.W., et al., "Synthesis of EnantiomericallyPure (2'R,5'S)—(–)–1+[2–(hydroxymethyl)–oathiolan–5–yl]Cytosine . . . ," *J. Org. Chem.* 57:2217–2219 (1992).

Kukhanova, M., et al., "L– and D–Enantiomers of 2',3'–Dideoxycytidine . . . ," *J. Bio. Chem.* 270:39 23056–23059 (1995).

Belleau, B., et al., "Design and Activity of a Novel Class of Nucleoside Analogs . . . ," *Int. Conf. on AIDS,* Montreal, Quebec, Canada, Jun. 4–9, 1989.

Bouffard, D.Y., et al., "Kinetic Studies on 2',2'–Difluorodeoxycytidine(gemcitibine) . . . ," *Biochem. Pharmacol.* 45:1857–1861 (1993).

Carter, et al., "Activities of (–)–Carbovir and 3'–Azido–3'–Deoxythmidine Against . . . ," *Antimicrobial Agents and Chemotherapy,* 36(6):1297–1300 (1990).

Chang, C–N., et al., "Biochemical Pharmacology of (+) and (–)–2',3'–Dideoxy–3'thioacytidine as Anti–Hepatitis B Virus Agents," *J. Biol. chem.* 267:22414–22420 (1992).

Chang, Chein–Neng et al., "Deoxycytidine Deaminase–resistant Steroisomer . . . ," *J. Bio.Chem.,* 357(20):13938–13942 (1992).

Chang, Chungming, et al., "Production of Hepatitis B Virus in vitro by Transient Expression . . . ," *the EMBO J.* 6(3):675–680 (1987).

Chen, Chin–Ho, et al., "Delayed Cytotoxicity and Selective Loss of Mitochondrial DNA in Cells . . . ," *J. Bio. Chem.* 264(20):11934–11937 (1989).

Cheng, Y.C., et al., "Human Deoxycytidine Kinase Purification and Characterization . . . ," *Biochem. Biophys. Acta.* 481:481–492 (1977).

Chottiner, E.G., "Cloning and Expression of Human Deocytctidine Kinase cDNA," *proc. Natl. Sci. USA,* 88:1531–1535 (1991).

(List continued on next page.)

*Primary Examiner*—Jerome D. Goldberg
*Attorney, Agent, or Firm*—Coleman and Sudol

[57] ABSTRACT

(–)-(2S,4S)-1-(2-Hydroxymethyl-1,3-dioxolan-4-yl) cytosine (also referred to as (–)-OddC) and its use to treat cancer in animals, including humans.

19 Claims, 4 Drawing Sheets

OTHER PUBLICATIONS

Chu, C.K., et al., "An Efficient Total Synthesis of 3'-Azido-3'-Deoxythiymidine (AZT) and 3'-Azido-2', 3'-Dideoxyuridine (AZDDU, CS-87) . . . ," *Tetrahedron Lett.* 5349 (1988).

Chu, et al., "Comparative Activity of 2',3'-Saturated and Unsaturated Pyrimidine and Purine Nucleosides . . . ," *Biochem. Pharm*, 37(19):3543–3548 (1988).

Chu, et al., "Structure–Activity Relationships of Pyrimidine Nucleosides as Antiviral Agents . . . ," *J. Med. Chem.* 32:612 (1989).

Chu, C.K., et al., "2'-Fluoro-5-Methyl-β-L-Arabinofuranosyluridine (L-FMAU) as a Novel Antiviral Agent for Hepatitis B . . . ," *Antimicrob. Agents. Chemother.*

Coates, J., et al., "The Separated Enaniomers of 2'-deoxy-3'-thiacytidine (BCH-189) . . . ," *Antimicrob. Agents Chemother*, 36:202–205 (1992).

Cretton, E., et al., "Catabolism of 3'-Azido-3'-Deoxythymidine in Heptaocytes and Liver Microsomes . . . ," *Molecuilar Pharmacology*, 39:258–266 (1991).

Cretton, E., et al., "Pharmokinetics of 3'-Azido-3'-Dexoythymidine . . . ," *Antimicrobial Agents and Chemotherapy*, 35(5):801–807 (1991).

Di Bisceglie, Adrian M., Rutsgi, Vinod K. et al., "Hepatocellular Carcinoma," NIH Conference, *Annals of Internal Medicine*, 108:390–401 (1988).

Doong, Shin–Lian., et al., "Inhibition of the Replication of Hepatitis B Virus in vitro . . . ," *Natl. Acad. Sci. USA*, 88:8495–8499 (1991).

Evans, David A., et al., "New Procedure for the Direct Generation of Titanium Enolates . . . ," *J. Am. Chem. Soc.*, 112:8215–8216 (1990).

Finlay, G.J., et al., "A Semiautomated Microculture Method for Investigating Exponentially Growing Carcinoma Cells," *Anal. Biochem.*, 139:272–277 (1984).

Furman, et al., "The Anti–Hepatitis B Virus Activities, Cytotoxicities, and Anabolic Profiles . . . ," *Antim. Agents and Chemo.*, 36(12):2686–2692 (1992).

Ganem, Don et al., "The Molecular Biology of the Hepatitis B Viruses," *Ann. Rev. Biochem.*, 56:651–693 (1987).

Gosselin, G., "Enantiomeric 2',3'-Deoxycytidine Derivatives are Potent Human Immunodeficiency Virus Inhibitors in Cell Culture," *C.R. Acad. Sci. Paris Sci. Vie*, 317:85–89 (1994).

Jeong, L., et al., "Asymmetric Synthesis and Biological Evaluation of β-L-(2R,5S)- and a-L-l(2R-5R)-1,3-Oxathiolane-Pyrimidine and –Purine Nucleosides and Potential Anti–HIV Agents," *J. Med. Chem.*, vol. 36 (1993).

Kassianides, Chris, et al., "Inhibition of Duck Hepatitis B Virus Replication by 2',3'-Dideoxycytidine," *Gastroenterology*, 33:6899–6902 (1992).

Kim, H.O., et al., "Potent Anti–HIV and Anti–HBV Activities of (−)-L-β-Dioolane-C . . . ," *Tetrahedron Lett.*, 33:6899–6902 (1992).

Kim, H.O., et al., "L-β-(2S,4S)-and L-α-(2S, 4R)-Dioxolanyl Nucleosides as Potential Anti–HIV Agents . . . ," *J. Med. Chem.*, 1993, 36, 519–528.

Kim, H.O., et al., "1,3-Dioxolanylpurine Nucelosides (2R, 4R) and (2R,4S) with Selective Anti–HIV-1 Activity . . . ," *J.Med.Chem.* 1993, 36, 30–37.

Krenistsky, T.A., et al., "3'-Amino-2',3'-Dideoxyribonucleosides of Some Pyrimindines: Synthesis and Biological Activities," *J. Med. Chem.*, 26 (1983).

Lee, Bonita, et al., "In Vitro and In Vivo Comparison of the Abilities of Purine and . . . ," *Antimicrobial Agents and Chemotherapy*, 33(3):336–339 (1989).

Lin, T.S., et al., "Antiviral Activity of 2',3'-Dideoxy-β-L-5-fluorocytidiine(β-L-FddC) Against Hepatitis B Virus . . . ," 1:65–68 (1991).

Lin, et al., "Potent and Selective In Vitro Activity of 3'-Deoxythmindine-2-Ene-. . . ," *Biochem. Pharm.*, 36(17):2716 (1987).

Mansuri, M.M., et al., "Preparation of the Geometric isomers of DDC, DDA, D4C, and D4T . . . ," *Bioorg. Med. Chem. Lett.* 1:65–68 (1991).

Matthes, E., et al., "Potent Inhibition of Hepatitis B Virus Production In Vitro by Modified . . . ," *Anti. Agents and Chemot*,34(10):1986–1990 (1990).

Miller, Roger H., et al., "Common Evolutionary Origin of Hepatitis B Virus and Retroviruses," *Proc. Natl. Acad. Sci. USA*, 83:2531–2535 (1986).

Mitsuya, H., et al., "3'-Azido-3'-Deoxythymidine (BW A 509U): An Antiviral Agent that Inhibits . . . ," *Proc. Natl. Acad. Sci., USA*, 82:7097–7100 (1985).

Mitsuya, H., et al., "Rapid in Vitro Systems for Assessing . . . ," *AIDS: Modern Concepts and Therapeutic Challenges*, S. Broder, Ed. p. 303, Marcel–Dekker, New York (1987).

Mitsuya, H., et al., "Molecular Targets for AIDS Therapy," *Science*, vol. 249, pp. 1533–1544 (1990).

Norbeck, D., et al., "A New 2',3'-Dideoxynucleoside Prototype with In Vitro Activity Against HIV," *Tetrahedron Lett.*, pp. 6263–6266 (1989).

Okabem, M., et al., "Synthesis of the Dideoxynucleosides ddC and CNT . . . ," *J. Org. Chem.*, 53(20):4780–4786 (1988).

Ometto, M., et al., :In vitro Biochemical Tests to Evaluate the Response to Therapy of Acaute Leukemia with . . . ,*Semin. Oncol.* 14: 231–237 (1987).

Richman, D. D., et al., "the Toxicity of Azidothymidine (AZT) in the Treatment of Patients with AIDS . . . ," *N. Eng. J. Med.*, 317:192 (1987).

Satsumabayashi, S. et al., "The Synthesis of 1,3–Oxathiolane-5-one Derivatives,", *Bull, Chem. Soc. Japan*, 45:913 (1972).

Schinazi, R.F., et al., "Activities of the Four Optical Isomers of 2',3'-Dideoxy-3'-Thiacytidine . . . ," *Antimic. Agents & Chemo.* 36(3):672–676 (1992).

Schinazi, R.F., et al., "Insights into HIV Chemotherapy," *AIDS Research and Human Retroviruses* 8(6):963–990 (1992).

Schinazi, R.F., et al., "Pharmacokinetics and Metabolism of Racemic 2',3'-Dideoxy-5-Fluoro-3'-Thiacytidine in Rhesus Monkeys," *Antimicrobial Agents and Chemotherapy* 36(11):2432–2438 (1992).

Schinazi, R.F., et al., "Selective Inhibition of Human Immunodeficiency Viruses . . . ," *Antim. Agents and Chemo.* 36(11):2423–2431 (1992).

Schinazi, R.F., et al., "Substrate Specificity of *Escherichia Coli* Thymidine Phosphorylase for Pyrimidine . . . ", *Bioc. Pharm.* 44(2):199–204 (1992).

Sells, Mary Ann, et al, "Production of Hepatitis B Virus Particles in Hep G2 Cells . . . ," *Proc. Natl. Acad. Sci. USA*, 84:1005–1009 (1987).

Soudeyns, H., et al., "Anti–Human Immunodeficiency Virus Type 1 Activity and In Vitro Toxicity of 2'–Deoxy–3'–Thiacytidine . . . ,", *Antimicrobial Agents and Chemotherapy*, 35(7):1386–1990 (1991).

Sterzycki, R.Z., et al., "Synthesis and Anti–HIV Activity of Several 2'–Fluoro–Containing Pyrimidine Nucleosides," *J. Med. Chem.*, 33(8):2150–2157 (1990).

Storer, R., et al., "The Resolution and Absolute Stereochemistry of the Enantiomeris of cis–1–2–(Hydromethyl)–1,3–Oxathiolan–5–yl)cytosine . . . ," *Nucleosides & Nucleotides*, 12(2):225–236 (1993).

Sureau, C., et al., "Preparation of Hepatitis B Virus by a Differentiated Human Hepatoma Cell Line After Transfection with Cloned Circular HBV DNA," *Cell*, 47:37–47 (1986).

Tsurimoto, Toshiki et al., "Stable Expression and Replication of Hepatitis B Virus Genome . . . ," *Proc. Natl. Acad. Sci. USA*, 84:444–448 (1987).

Volk, Wesley A., editor, "Hepatitis," *Essentials of Medical Microbiology*, J.B. Lippincott Company, (Philadelphia/Toronto), 2nd Ed., pp. 609–618 (1982).

Vorbrüggen, et al, "Nucleoside Synthesis with Trimethylsilyl Triflate and Perchlorate as Catalysts," *Chem. Ber.*, 114:1234–1255 (1981).

Wilson, L.J., et al., "The Synthesis and Anti–HIV Activity of Pyrimidine Dioxolanyl Nucleosides," *Bioorganic & Medicinal Chemistry Letters*, 3(2):169–174 (1993).

Wilson, L.J., et al., "A General Method for Controlling Glycosylation Stereochemistry in the Synthesis . . . ," *Tetrahedron Lett.*, 31(13):1815–1818 (1990).

World Health Organization, "Progress in the Control of Viral Hepatits: Memorandum from a WHO Meeting," *Bulletin of the World Health Organization*, 66(4):443–455 (1988).

Yokota et al., "Comparative Activities of Several Nucleoside Analogs Against Duck . . . ," *Antimicrobial Agents and Chemotherapy*, 34:1326–1330 (1990).

Zhu, Zhou, et al., "Cellular Metabolism of 3'–Azido–2',3'–Dideoxyuridine with Formation of 5'–)–Diphophoshexase . . . " *Molecular Pharmacology*, 38:929–938 (1990).

COMPOUNDS AND METHODS FOR THE TREATMENT OF CANCER

This application is a continuation-in-part of U.S. application Ser. No. 07/937,845, filed on Oct. 19, 1992, by Yung-Chi Cheng, Chung K. Chu, Hea O. Kim, and Kirupathevy Shanmuganathan, which is entitled "Method of Treating or Preventing Hepatitis B Virus" which claims priority to PCT/US92/03144, filed on April 16, 1992.

GOVERNMENT RIGHTS

The U.S. government has rights in this invention by virtue of Grant No. CA-44358 from the National Cancer Institute (NIH).

FIELD OF THE INVENTION

This invention is in the area of medicinal chemistry, and in particular is (−)-(2S,4S)-1-(2-hydroxymethyl-1,3-dioxolan-4-yl)cytosine (also referred to as (−)-OddC) and its use to treat cancer in animals, including humans.

BACKGROUND OF THE INVENTION

A tumor is an unregulated, disorganized proliferation of cell growth. A tumor is malignant, or cancerous, if it has the properties of invasiveness and metastasis. Invasiveness refers to the tendency of a tumor to enter surrounding tissue, breaking through the basal laminas that define the boundaries of the tissues, thereby often entering the body's circulatory system. Metastasis refers to the tendency of a tumor to migrate to other areas of the body and establish areas of proliferation away from the site of initial appearance.

Cancer is now the second leading cause of death in the United States. Over 8,000,000 persons in the United States have been diagnosed with cancer, with 1,208,000 new diagnoses expected in 1994. Over 500,000 people die annually from the disease in this country.

Cancer is not fully understood on the molecular level. It is known that exposure of a cell to a carcinogen such as certain viruses, certain chemicals, or radiation, leads to DNA alteration that inactivates a "suppressive" gene or activates an "oncogene". Suppressive genes are growth regulatory genes, which upon mutation, can no longer control cell growth. Oncogenes are initially normal genes (called prooncogenes) that by mutation or altered context of expression become transforming genes. The products of transforming genes cause inappropriate cell growth. More than twenty different normal cellular genes can become oncogenes by genetic alteration. Transformed cells differ from normal cells in many ways, including cell morphology, cell-to-cell interactions, membrane content, cytoskeletal structure, protein secretion, gene expression and mortality (transformed cells can grow indefinitely).

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

Cancer is now primarily treated with one or a combination of three types of therapies: surgery, radiation, and chemotherapy. Surgery involves the bulk removal of diseased tissue. While surgery is sometimes effective in removing tumors located at certain sites, for example, in the breast, colon, and skin, it cannot be used in the treatment of tumors located in other areas, such as the backbone, nor in the treatment of disseminated neoplastic conditions such as leukemia.

Chemotherapy involves the disruption of cell replication or cell metabolism. It is used most often in the treatment of leukemia, as well as breast, lung, and testicular cancer.

There are five major classes of chemotherapeutic agents currently in use for the treatment of cancer: natural products and their derivatives; anthracyclines; alkylating agents; anti-proliferatives (also called antimetabolites); and hormonal agents. Chemotherapeutic agents are often referred to as antineoplastic agents.

The alkylating agents are believed to act by alkylating and cross-linking guanine and possibly other bases in DNA, arresting cell division. Typical alkylating agents include nitrogen mustards, ethyleneimine compounds, alkyl sulfates, cisplatin, and various nitrosoureas. A disadvantage with these compounds is that they not only attack malignant cells, but also other cells which are naturally dividing, such as those of bone marrow, skin, gastro-intestinal mucosa, and fetal tissue.

Antimetabolites are typically reversible or irreversible enzyme inhibitors, or compounds that otherwise interfere with the replication, translation or transcription of nucleic acids.

Several synthetic nucleosides have been identified that exhibit anticancer activity. A well known nucleoside derivative with strong anticancer activity is 5-fluorouracil. 5-Fluorouracil has been used clinically in the treatment of malignant tumors, including, for example, carcinomas, sarcomas, skin cancer, cancer of the digestive organs, and breast cancer. 5-Fluorouracil, however, causes serious adverse reactions such as nausea, alopecia, diarrhea, stomatitis, leukocytic thrombocytopenia, anorexia, pigmentation, and edema. Derivatives of 5-fluorouracil with anti-cancer activity have been described in U.S. Pat. No. 4,336,381, and in Japanese patent publication Nos. 50-50383, 50-50384, 50-64281, 51-146482, and 53-84981.

U.S. Pat. No. 4,000,137 discloses that the peroxidate oxidation product of inosine, adenosine, or cytidine with methanol or ethanol has activity against lymphocytic leukemia.

Cytosine arabinoside (also referred to as Cytarabin, araC, and Cytosar) is a nucleoside analog of deoxycytidine that was first synthesized in 1950 and introduced into clinical medicine in 1963. It is currently an important drug in the treatment of acute myeloid leukemia. It is also active against acute lymphocytic leukemia, and to a lesser extent, is useful in chronic myelocytic leukemia and non-Hodgkin's lymphoma. The primary action of araC is inhibition of nuclear DNA synthesis. Handschumacher, R. and Cheng, Y., "Purine and Pyrimidine Antimetabolites", *Cancer Medicine,* Chapter XV-1, 3rd Edition, Edited by J. Holland, et al., Lea and Febigol, publishers.

5-Azacytidine is a cytidine analog that is primarily used in the treatment of acute myelocytic leukemia and myelodysplastic syndrome.

2-Fluoroadenosine-5'-phosphate (Fludara, also referred to as FaraA)) is one of the most active agents in the treatment of chronic lymphocytic leukemia. The compound acts by inhibiting DNA synthesis. Treatment of cells with F-araA is associated with the accumulation of cells at the G1/S phase boundary and in S phase; thus, it is a cell cycle S phase-specific drug. Incorporation of the active metabolite, F-araATP, retards DNA chain elongation. F-araA is also a potent inhibitor of ribonucleotide reductase, the key enzyme responsible for the formation of dATP.

2-Chlorodeoxyadenosine is useful in the treatment of low grade B-cell neoplasms such as chronic lymphocytic leukemia, non-Hodgkins' lymphoma, and hairy-cell leukemia. The spectrum of activity is similar to that of Fludara. The compound inhibits DNA synthesis in growing cells and inhibits DNA repair in resting cells.

Although a number of chemotherapeutic agents have been identified and are currently used for the treatment of cancer, new agents are sought that are efficacious and which exhibit low toxicity toward healthy cells.

Therefore, it is an object of the present invention to provide compounds that exhibit anti-tumor, and in particular, anti-cancer, activity.

It is another object of the present invention to provide pharmaceutical compositions for the treatment of cancer.

It is further object of the present invention to provide a method for the treatment of cancer.

SUMMARY OF THE INVENTION

A method and composition for the treatment of cancer in humans and other host animals is disclosed that includes administering an effective amount of (−)-(2S,4S)-1-(2-hydroxymethyl-1,3-dioxolan-4-yl)cytosine, a pharmaceutically acceptable derivative thereof, including a 5' or $N^4$ alkylated or acylated derivative, or a pharmaceutically acceptable salt thereof, optionally in a pharmaceutically acceptable carrier.

It is believed that (−)-(2S,4S)-1-(2-hydroxymethyl-1,3-dioxolan-4-yl)cytosine is the first example of an "L"-nucleoside that exhibits anti-tumor activity. (−)-(2S,4S)-1-(2-Hydroxymethyl-1,3-dioxolan-4-yl)cytosine has the structure illustrated in Formula I.

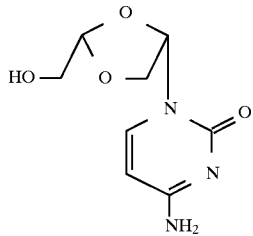

It has been discovered that (−)-(2S,4S)-1-(2-hydroxymethyl-1,3-dioxolan-4-yl)cytosine exhibits significant activity against cancer cells and exhibits low toxicity toward healthy cells in the host. Nonlimiting examples of cancers that can be treated with this compound include lung, colorectal, breast, prostate, bladder, pancreas, ovarian, leukemia, and lymphoma.

DETAILED DESCRIPTION OF THE INVENTION

Figure 1:
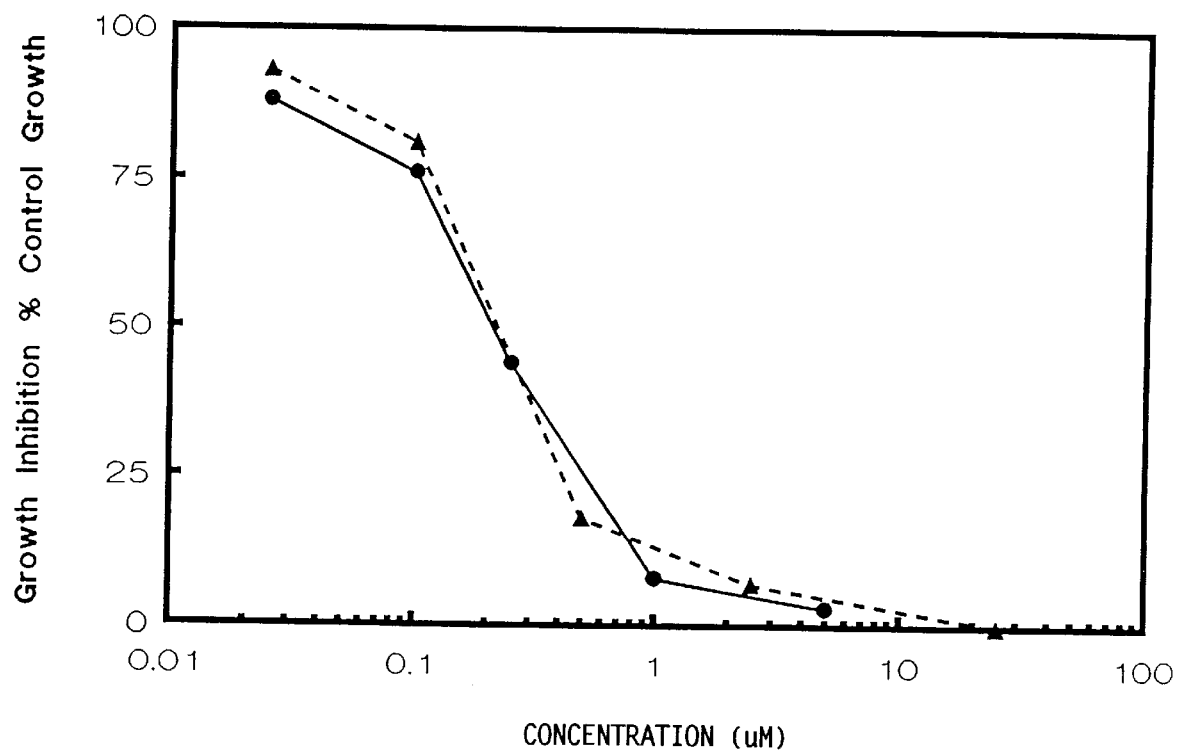
FIG. 1 indicates the $ID_{50}$ of (−)-OddC and a combination of (−)-OddC+THU (tetrahydrouridine, a cytidine deaminase inhibitor) on colon cancer cells. The graph plots growth inhibition as a percentage of control growth vs. concentration ($\mu$M). In the graph, the data for (−)-OddC alone is represented by (●) and the data for (−)-OddC+THU is represented by (- - ▲ - -).

The invention as disclosed herein is a method and composition for the treatment of tumors, and in particular, cancer in humans or other host animals, that includes administering an effective amount of (−)-(2S,4S)-1-(2-hydroxymethyl-1,3-dioxolan-4-yl)cytosine, a physiologically acceptable derivative of the compound, including a 5' or $N^4$ alkylated or acylated derivative, or a physiologically acceptable salt thereof, optionally in a pharmaceutically acceptable carrier.

(−)-(2S,4S)-1-(2-Hydroxymethyl-1,3-dioxolan-4-yl) cytosine is referred to as an "L"-nucleoside. Since the 2 and 5 carbons of the dioxolane ring are chiral, their nonhydrogen substituents ($CH_2OH$ and the cytosine base, respectively) can be either cis (on the same side) or trans (on opposite sides) with respect to the dioxolane ring system. The four optical isomers therefore are represented by the following configurations (when orienting the dioxolane moiety in a horizontal plane such the oxygen in the 3-position is in front): cis (with both groups "up", which corresponds to the configuration of naturally occurring nucleosides, referred to as a "D"-nucleoside), cis (with both groups "down", which is the non-naturally occurring configuration, referred to as an "L"-nucleoside), trans (with the C2 substituent "up" and the C5 substituent "down"), and trans (with the C2 substituent "down" and the C5 substituent "up"). It is believed that (−)-(2S,4S)-1-(2-hydroxymethyl-1,3-dioxolan-4-yl) cytosine is the first example of an "L"-nucleoside that exhibits anti-tumor activity. This is surprising, in light of the fact that this "L" nucleoside configuration does not occur in nature.

The active compound can be administered as any derivative that upon administration to the recipient, is capable of providing directly or indirectly, the parent (−)-OddC compound, or that exhibits activity itself. Nonlimiting examples are the pharmaceutically acceptable salts (alternatively referred to as "physiologically acceptable salts") of (−)-OddC, and the 5' and $N^4$ acylated or alkylated derivatives of the active compound (alternatively referred to as "physiologically active derivatives"). In one embodiment, the acyl group is a carboxylic acid ester in which the non-carbonyl moiety of the ester group is selected from straight, branched, or cyclic alkyl (typically $C_1$ to $C_{18}$, and more typically $C_1$ to $C_5$), alkaryl, aralkyl, alkoxyalkyl including methoxymethyl, aralkyl including benzyl, aryloxyalkyl such as phenoxymethyl; aryl including phenyl optionally substituted with halogen, $C_1$ to $C_4$ alkyl or $C_1$ to $C_4$ alkoxy; sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group.

Specific examples of pharmaceutically acceptable derivatives of (−)-OddC include, but are not limited to:

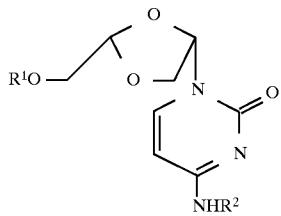

wherein $R_1$ and $R_2$ are independently selected from the group consisting of alkyl and acyl, specifically including but not limited to methyl, ethyl, propyl, butyl, pentyl, hexyl, isopropyl, isobutyl, sec-butyl, t-butyl, isopentyl, amyl, t-pentyl, 3-methylbutyryl, hydrogen succinate, 3-chlorobenzoate, cyclopentyl, cyclohexyl, benzoyl, acetyl, pivaloyl, mesylate, propionyl, butyryl, valeryl, caproic, caprylic, capric, lauric, myristic, palmitic, stearic, oleic, and amino acids including but not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl, and wherein one of $R_1$ and $R_2$ can be H.

(−)-OddC or its derivatives can be provided in the form of pharmaceutically acceptable salts. As used herein, the term pharmaceutically acceptable salts or complexes refers to salts or complexes of (−)-OddC that retain the desired biological activity of the parent compound and exhibit minimal, if any, undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, sodium, potassium, and the like, or with an organic cation formed from N,N-dibenzylethylenediamine, ammonium, or ethylenediamine; or (c) combinations of (a) and (b); e.g., a zinc tannate salt or the like.

Modifications of the active compound, specifically at the $N^4$ and 5'-O positions, can affect the solubility, bioavailability and rate of metabolism of the active species, thus providing control over the delivery of the active species. Further, the modifications can affect the anticancer activity of the compound, in some cases increasing the activity over the parent compound. This can easily be assessed by preparing the derivative and testing its anticancer activity according to the methods described herein, or other method known to those skilled in the art.

II. Preparation of the Active Compounds (−)-OddC can be prepared according to the method disclosed in detail in PCT International Publication No. WO 92/18517, published on Oct. 29, 1992, or by the method disclosed in Scheme 1 and working examples 1–7 provided below, or by any other method known to those skilled in the art.

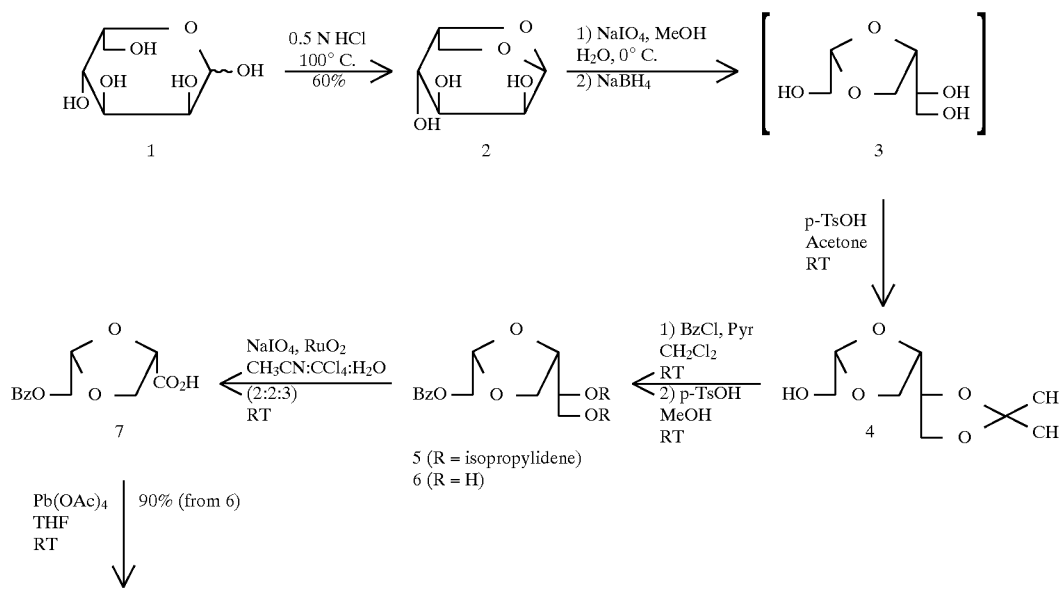

-continued

Scheme 1: Synthesis of (−)-OddC

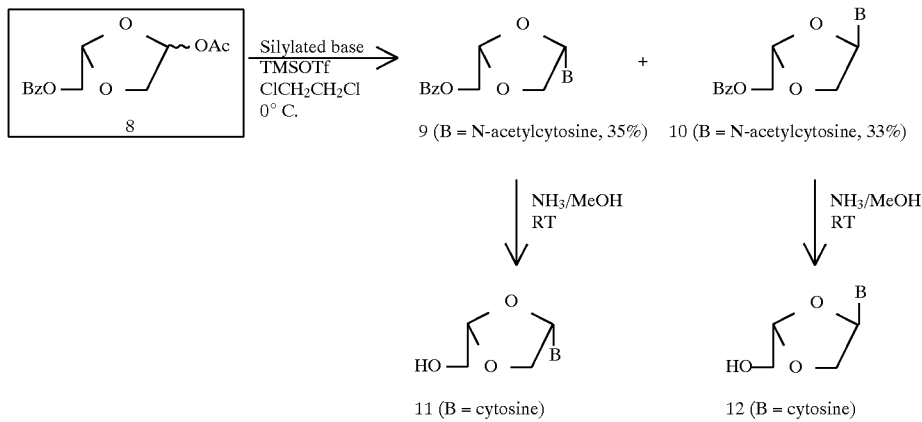

EXAMPLE 1

Preparation of 6-Anhydro-L-gulose

6-Anhydro-L-gulose was prepared in one step from L-gulose by the treatment of L-gulose with an acid, e.g., 0.5N HCl, in 60% yield (Evans, M. E., et al., *Carbohydr. Res.* (1973), 28, 359). Without selective protection, as was done before (Jeong, L. S. et al. *Tetrahedron Lett.* (1992), 33, 595 and Beach, J. W. et al. *J. Org. Chem.* (1992,in press), (2) was directly converted to dioxolane triol (3) by oxidation with $NaIO_4$, followed by reduction with $NaBH_4$, which without isolation, was converted to isopropylidene derivative (4). Benzoylation to (5), deprotection to (6), and oxidation of diol (6) gave the acid (7). Oxidative decarboxylation of (7) with $Pb(OAc)_4$ in dry THF gave the acetate (8), the key intermediate in good yield. The acetate was condensed with the desired pyrimidines (e.g., silylated thymine and N-acetylcytosine) in the presence of TMSOTf to afford an α,β-mixture, which was separated on a silica gel column to obtain the individual isomers (9 and 10). Debenzoylation with methanolic ammonia gave the desired (−)-OddC (11).

EXAMPLE 2

Preparation of (−)-1,6-Anhydro-α-L-gulopyranose (2)

A mixture of L-gulose (1) (33 g,0.127 mol) and 0.5N HCl (330 mL, 0.165 mol) was refluxed for 20 hours. The mixture was cooled and neutralized to pH 6 by a resin (Dowex-2, $HCO_3$-form) with air bubbling. The resin was recycled by washing with 10% HCl, water, methanol, water and saturated $NaHCO_3$ solution. The reaction mixture was filtered and the resin was washed with water (500 mL). The combined filtrate was concentrated to dryness and dried in vacuo overnight. The residue was purified over a column (5 cm depth, silica gel, mesh, $CHCl_3$—$CH_3OH$, 10:1) to give a slightly yellow solid, which was recrystallized from absolute alcohol to give a colorless solid (2) [$R_f$=0.43 ($CHCl_3$—$CH_3OH$, 5:1), 7.3 g, 35.52%]. The L-gulose $R_f$=0.07, 11 g) obtained was recycled to give (2) (5 g, total yield 60%):mp 142.5°–145° C.; $^1$H NMR (DMSO-$d_6$) δ6 3.22–3.68 (m, 4H, H-2, -3, -4 and -6a), 3.83 (d,$J_{6b,6a}$=7.25 Hz, 1H, $H_b$-6), 4.22 (pseudo t, $J_{5,6a}$=4.61 and 4.18 Hz, H, H-5), 4.46 (d, $J_{2\text{-}OH,2}$=6.59 Hz, 1H, 2-OH, exchangeable with $D_2O$), 4.62 (d, $J_{3\text{-}OH,3}$=5.28 Hz, 1H, 3-OH, exchangeable with $D_2O$), 5.07 (d, $J_{4\text{-}OH,4}$=4.84 Hz, 1H, 4-OH, exchangeable with $D_2O$), 5.20 (d, $J_{1,2}$=2.19 Hz, 1H, H-1). $[\alpha]_D^{25}$-50.011 (c, 1.61, $CH_3OH$).

EXAMPLE 3

Preparation of (−)-(1'S,2S,4S)-4-(1,2-Dihydroxyethyl-1,2-O-Isopropylidene)-2-hydroxymethyl)-dioxolane (4)

A solution of $NaIO_4$ (22.36 g, 0.1 mol) in water (300 mL) was added in a dropwise manner over 10 minutes to a solution of (2) (11.3 g, 0.07 mol) in methanol (350 mL) cooled to 0° C. The mixture was stirred mechanically for 15 minutes. $NaBH_4$ (7.91 g, 0.21 mol) was added to this mixture and the reaction mixture was stirred for 10 minutes at 0° C. The white solid was filtered off and the solid was washed with methanol (300 mL). The combined filtrate was neutralized by 0.5N HCl (~200 mL) and concentrated to dryness. The residue was dried in vacuo overnight. The syrupy residue was triturated with methanol-acetone (1:5 , 1200 mL) using a mechanical stirrer (5 hours) and the white solid (1st.) was filtered off. The filtrate was concentrated to dryness and the residue was dissolved in acetone (500 mL) and followed by p-toluene sulfonic acid (6.63 g, 0.035 mol). After stirring for 6 hours, the mixture was neutralized by triethylamine, the solid (2nd.) was filtered off and the filtrate was concentrated to dryness. The residue was dissolved in ethyl acetate (350 mL) and washed with water (50 mL×2), dried ($MgSO_4$), filtered, and evaporated to give crude (4) (3.6 g) as a yellowish syrup. The water layer was concentrated to dryness and dried in vacuo. The solid obtained (1st and 2nd) was combined with the dried water layer and recycled by stirring for 1 hour in 10% methanol-acetone (900 mL) and p-toluene sulfonic acid (16 g, 0.084 mol) to yield crude (4) (5.6 g). The crude (4) was purified by a dry column over silica gel ($CH_3OH$—$CHCl_3$, 1%–5%) to give (4) [$R_f$=0.82($CHCl_3$—$CH_3OH$, 10:1), 8.8 g, 61.84%] as a colorless oil. $^1$H NMR(DMSO-$d_6$) δ1.26 and 1.32 (2×S, 2×3 H, isopropylidene), 3.41 (dd, $J_{CH2OH,OH}$=6.04 Hz, $J_{CH2OH,2}$=3.96 Hz, 2H, $CH_2OH$), 3.56–4.16 (m, 6H, H-4, -5, -1' and -2'), 4.82 (t, $J_{OH,CH2}$=6.0 Hz, 1 H, $CH_2OH$, exchangeable with $D_2O$), 4.85 (t, $J_{2OH,CH2OH}$=3.96 Hz, 1H, H-2).$[\alpha]_D^{25}$-12.48 (c, 1.11, $CHCl_3$), Anal, Calcd for $C_9H_{16}O_5$:C,52.93; H, 7.90. Found:C,52.95; H, 7.86.

EXAMPLE 4

Preparation of (+)-(1'S,2S,4S)-4-(1,2-Dihydroxymethyl-1,2-O-Isopropylidene)-2-(O-benzoyloxymethyl)-dioxolane (5)

Benzoyl chloride (6.5 mL, 0.056 mol) was added in a dropwise manner to a solution of (4) (8.5 g, 0.042 mol) in pyridine-CH$_2$Cl$_2$ (1:2, 120 mL) at 0° C. and the temperature was raised to room temperature. After stirring for 2 hours, the reaction was quenched with methanol (10 mL) and the mixture was concentrated to dryness in vacuo. The residue was dissolved in CH$_2$Cl$_2$ (300 mL) and washed with water (100 mL×2), brine, dried (MgSO$_4$), filtered, evaporated to give a yellowish syrup, which was purified by silica gel column chromatography (EtOAc-Hexane 4%–30%) to yield (5) [R$_f$=0.45 (Hexane-EtOAc, 3:1), 10.7 g, 83.4%] as a colorless oil. 1H NMR (CDCl$_3$) δ1.35 and 1.44 (2×s, 2×3H, isopropylidene) 3.3–4.35 (m 6H, H-4, -5, -1' and -2'), 4.44 (d, J=3.96 Hz, 2H, CH$_2$—OBz), 5.29 (t, J=3.74 Hz, 1H, H-2), 7.3–7.64, 8.02–8.18 (m, 3H, 2H, —OBz). [α]$_D^{25}$+ 10.73(c,1.75,CH$_3$OH).

Anal. Calcd for C$_{16}$H$_{20}$O$_6$:C,62.33;H,6.54. Found: C,62.39; H, 6.54.

EXAMPLE 5

Preparation of (+)-(1'S,2S,4S)-4-(1,2-Dihydroxyethyl)-2-(O-benzoyloxymethyl)-dioxolane (6)

A mixture of (5) (5.7 g. 0.018 mol) and p-toluene sulfonic acid (1.05 g. 0.0055 mol) in methanol (70 mL) was stirred at room temperature for 2 hours. The reaction was not completed, so the solvent was evaporated to half of the original volume and additional methanol (50 mL) and p-toluene sulfonic acid (0.7 g, 3.68 mmol) were added. After stirring for one more hour, the reaction mixture was neutralized with triethyl amine and the solvent was evaporated to dryness.

The residue was purified by silica gel column chromatography (Hexane-EtOAC, 10%–33%) to give (6) [R$_f$=0.15 (Hexane-EtOAc, 1:1), 4.92 g, 99.2%] as a colorless syrup $^1$H NMR (DMSO-d$_6$) ) δ3.43 (m, 2H, H-2'), 3.67–4.1 (m, 4H, H-4, -5 and -1'), 4.32 (d, J=3.73 Hz, 2H, CH$_2$—OBz), 4.60 (t,J=5.72 Hz, 2'-OH, exchangeable with D$_2$O), 5.23 (t, J=3.96 Hz, 1H, H-2), 7.45–7.7, 7.93–8.04 (m, 3H, 2H, —OBz), [α]$_D^{25}$+9.16 (c,1.01, CHCl$_3$).

Anal. Calcd for C$_{13}$H$_{16}$O$_6$:C,58.20; H,6.01. Found: c,58.02; H.6.04.

EXAMPLE 6

Preparation of (–)-(2S,4S) and (2S, 4R)-4-Acetoxy-2-(O-benzoyloxymethyl)-dioxolane (8)

A solution of NaIO$_4$ (10.18 g, 0.048 mol) in water (120 mL) was added to a solution of (6) (3.04 g, 0.011 mol) in CCl$_4$:CH$_3$CN (1:1, 160 mL), followed by RuO$_2$ hydrate (0.02 g). After the reaction mixture was stirred for 5 hours, the solid was removed by filtration over Celite and the filtrate was evaporated to ⅓ volume. The residue was dissolved in CH$_2$Cl$_2$ (100 mL) and the water layer was extracted with CH$_2$Cl$_2$ (100 mL×2). The combined organic layer was washed with brine (50 mL), dried (MgSO$_4$), filtered, evaporated to dryness and dried in vacuo for 16 hours to give crude (7) (2.6 g, 91%).

To a solution of crude (7) (2.6, 0.01 mol) in dry THF (60 mL) were added Pb(OAc)$_4$(5.48 g, 0.0124 mol) and pyridine (0.83 mL, 0.0103 mol) under N$_2$ atmosphere. The mixture was stirred for 45 minutes under N$_2$ and the solid was removed by filtration. The solid was washed with ethyl acetate (60 mL) and the combined organic layer was evaporated to dryness. The residue was purified by silica gel column chromatography (Hexane-EtOAc, 2:1) to yield (8) [R$_f$=0.73 and 0.79 (Hexane-EtOAc, 2:1), 1.9 g, 69.34%] as a colorless oil. $^1$H NMR (CDCl$_3$) δ1.998, 2.11 (2×s, 3H, —OAc), 3.93–4.33 (m, 2H, H-5), 4.43, 4.48 (2×d, J=3.73, 3.74 Hz, 2H, CH$_2$OBz), 5.46, 5.55 (2×t, J=4.18, 3.63 Hz, 1H, H-2), 6.42 (m, 1H, H-4), 7.33–759, 8.00–8.15 (m, 3H, 2H, —OBz).[α]$_D^{25}$-12.53 (c, 1.11, CHCl$_3$).

Anal. Calcd for C$_{13}$H$_{14}$O$_6$; C, 58.64; H, 5.30. Found C, 58.78; H, 5.34.

EXAMPLE 7

Preparation of (–)-(2S,4S)-1-[2-(benzoyl)-1,3-dioxolan-4-yl]cytosine(9) and (+)-(2S,4R)-1-[2-(benzyloxy)-1,3-dioxolan-4-yl)cytosine (10)

A mixture of N$^4$-acetylcytosine (1.24 g, 7.52 mmol) in dry dichloroethane (20 mL), hexamethyldisilazane (15 mL), and ammonium sulfate (cat. amount) was refluxed for 4 hours under a nitrogen atmosphere. The resulting clear solution was cooled to room temperature. To this silylated acetylcytosine was added a solution of (8) (1.0 g, 3.76 mmol) in dry dichloroethane (10 mL) and TMSOTf (1.46 mL 7.55 mmol). The mixture was stirred for 6 hours. Saturated NaHCO$_3$ (10 mL) was added and the mixture was stirred for another 15 minutes and filtered through a Celite pad. The filtrate was evaporated and the solid was dissolved in EtOAc and washed with water and brine, dried, filtered and evaporated to give the crude product. This crude product was purified on a silica column (5% CH$_3$OH/CHCl$_3$) to yield a pure α,β mixture of (9) and (10) (0.40 g, 30%) and the α,β mixture of (13) and (14) (0.48 g, 40%). The mixture of (14) was reacetylated for separation, the combined α,β mixture was separated by a long silica column (3% CH$_3$OH/CHCl$_3$) to yield (9) (0.414 g, 30.7%) and (10) (0.481 g, 35.6%) as foams. These foams were triturated with CH$_3$OH to obtain white solids. 9: UV (CH$_3$OH) λ max 298 nm; Anal. (C$_{17}$H$_{17}$N$_3$O$_8$) C, H, N. 10: UV (CH$_3$OH) λ max 298 nm.

EXAMPLE 8

Preparation of (–)-(2S,4S)-1-(2-Hydroxymethyl-1,3-dioxolan-4-yl)cytosine (11)

A solution of (9) (0.29 g, 0.827) in CH$_3$OH/NH$_3$ (50 mL, saturated at 0° C.) was stirred at room temperature for 10 hours. The solvent was evaporated and the crude (11) was purified on preparative silica plates (20% CH$_3$OH/CHCl$_3$) to give an oil. This was crystallized from CH$_2$Cl$_2$/hexane to give (11) (0.136 g, 77.7%) as a white solid. UV λ max 278.0 nm (ε 11967) (pH 2), 270.0 nm (ε 774) (pH 7), 269.0 nm (ε8379) (pH 11); Anal. (C$_8$H$_{11}$N$_3$O$_4$)C,H,N.

II. Pharmaceutical Compositions

Humans, equines, canines, bovines and other animals, and in particular, mammals, suffering from cancer can be treated by administering to the patient an effective amount of (–)-OddC or a pharmaceutically acceptable salt thereof optionally in a pharmaceutically acceptable carrier or diluent, either alone, or in combination with other known anticancer or pharmaceutical agents. This treatment can also be administered in conjunction with other conventional cancer therapies, such as radiation treatment or surgery.

These compounds can be administered by any appropriate route, for example, orally, parenterally, intravenously, intradermally, subcutaneously, or topically, in liquid, cream, gel, or solid form, or by aerosol form.

The active compound is included in the pharmaceutically acceptable carrier or diluent in an amount sufficient to deliver to a patient a therapeutically effective amount for the desired indication, without causing serious toxic effects in the patient treated. A preferred dose of the active compound for all of the herein-mentioned conditions is in the range from about 10 ng/kg to 300 mg/kg, preferably 0.1 to 100 mg/kg per day, more generally 0.5 to about 25 mg per kilogram body weight of the recipient per day. A typical topical dosage will range from 0.01–3% wt/wt in a suitable carrier.

The compound is conveniently administered in any suitable unit dosage form, including but not limited to one containing 1 to 3000 mg, preferably 5 to 500 mg of active ingredient per unit dosage form. A oral dosage of 25–250 mg is usually convenient.

The active ingredient is preferably administered to achieve peak plasma concentrations of the active compound of about 0.00001–30 mM, preferably about 0.1–30 $\mu$M. This may be achieved, for example, by the intravenous injection of a solution or formulation of the active ingredient, optionally in saline, or an aqueous medium or administered as a bolus of the active ingredient.

The concentration of active compound in the drug composition will depend on absorption, distribution, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered at once, or may be divided into a number of smaller doses to be administered at varying intervals of time.

Oral compositions will generally include an inert diluent or an edible carrier. They may be enclosed in gelatin capsules or compressed into tablets. For the purpose of oral therapeutic administration, the active compound or its pro-drug derivative can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a dispersing agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring. When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or enteric agents.

The active compound or pharmaceutically acceptable salt thereof can be administered as a component of an elixir, suspension, syrup, wafer, chewing gum or the like. A syrup may contain, in addition to the active compounds, sucrose as a sweetening agent and certain preservatives, dyes and colorings and flavors.

The active compound or pharmaceutically acceptable salts thereof can also be mixed with other active materials that do not impair the desired action, or with materials that supplement the desired action, such as other anticancer agents, antibiotics, antifungals, antiinflammatories, or antiviral compounds.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation can be enclosed in ampoules, disposable syringes or multiple dose vials made of glass or plastic.

If administered intravenously, preferred carriers are physiological saline or phosphate buffered saline (PBS).

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

Liposomal suspensions may also be pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the active compound are then introduced into the container. The container is then swirled by hand to free lipid material from the sides of the container and to disperse lipid aggregates, thereby forming the liposomal suspension.

III. Biological Activity

A wide variety of biological assays have been used and are accepted by those skilled in the art to assess anti-cancer activity of compounds. Any of these methods can be used to evaluate the activity of the compounds disclosed herein.

One common method of assessing activity is through the use of the National Cancer Institute's ("NCI") test panels of cancer cell lines. These tests evaluate the in vitro anti-cancer activity of particular compounds, and provide predictive data with respect to the use of tested compounds in vivo. Other assays include in vivo evaluations of the compound's effect on human or mouse tumor cells implanted into or grafted onto nude mice.

A. In Vivo Activity of (–)-OddC (–)-OddC was tested for anticancer activity in vivo against the P388 leukemia cell line and the C38 colon cancer cell line. Examples 8 and 9 provide the experimental details and results of these tests.

EXAMPLE 9

In Vivo Treatment of Leukemia P388 Cells With (–)-OddC $10^6$ Leukemia P388 cells were implanted ip to BDF1 mice obtained from Southern Research Institute, Alabama. L(–)-OddC was administered ip twice daily for five days starting one day after tumor cell implantation. Using this protocol, 75 mg/kg/dose was shown to be toxic to the mice.

Figure 3:
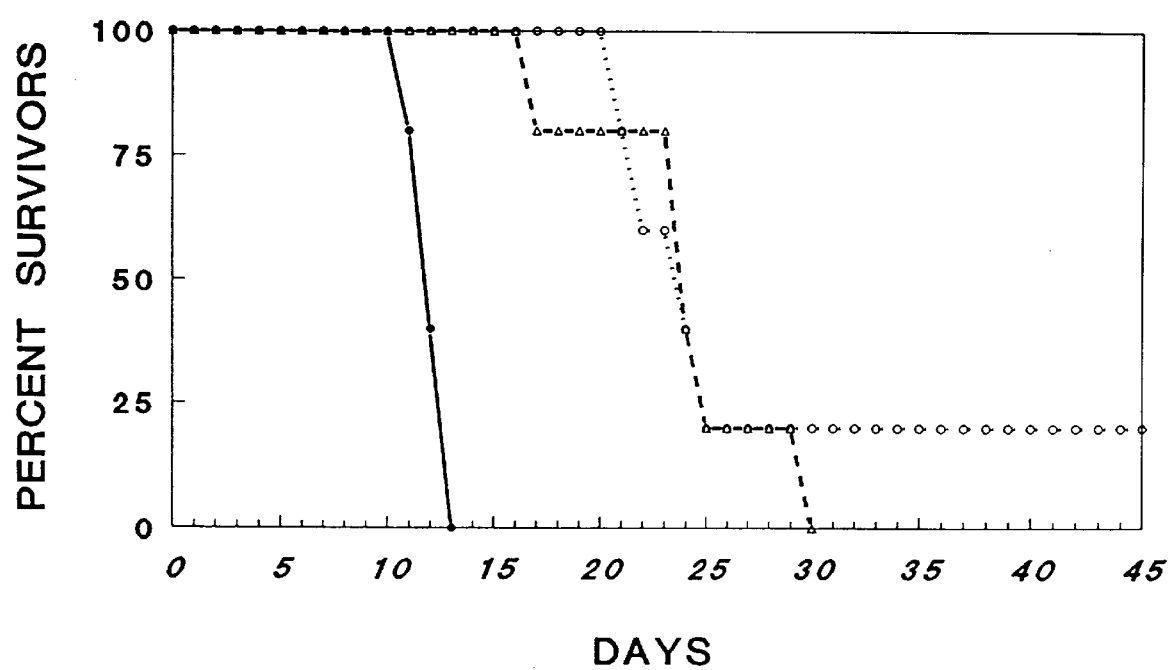
FIG. 3 indicates the survival rate of P388 leukemic mice that have been treated with (−)-OddC. The graph plots percentage of survival vs. days treated. Treatment of the mice occurred in days 1, 2, 3, 4 and 5. In the graph, the survival rate of the control (no administration of (−)-OddC) is represented by (●), the survival rate of those administered (−)-OddC at 25 mg/kgbid twice a day is represented by (- - Δ - -), and the survival rate of mice administered (−)-OddC once a day at 50 mg/kgbid is represented by (○).

FIG. 3 and Table 1 show the results of these studies. In FIG. 3, (●) represents the data for the control (untreated animals), (- - Δ - -) represents the survival rate of those administered (−)-OddC at 25 mg/kgbid twice a day, and (○) represents the survival rate of mice administered (−)-OddC once a day at 50 mg/kgbid. Of the six mice treated with 25 mg/kg/dose of (−)-OddC, there is one long term survivor, and the life span of the remaining five mice was increased by 103%.

TABLE 1

| Group | Dosage[a] (mg/kg) | Route | Mean Survival Time (days) | ILS[b] (%) | Death Time (day) | Cures[c]/ Total |
|---|---|---|---|---|---|---|
| Control | — | — | 13.3 | — | 11, 12, 13 13, 13, 18 | 0/6 |
| −OddC | 25 × 2 × 5 | ip | 27 | 103 | 18, 20, 22, 25, 33, 45 | 1/6 |

Inoculum: $10^6$ P388 cells were inoculated into each mouse ip on day 0
[a]: Treatment was given twice a day on days 1 to 5
[b]: Increased Life Span percent above control
[c]: Survivors equal or greater than 45 day life span

EXAMPLE 10

In Vivo Treatment of Colon 38 Tumor Cells With (1)-OddC

Figure 2:
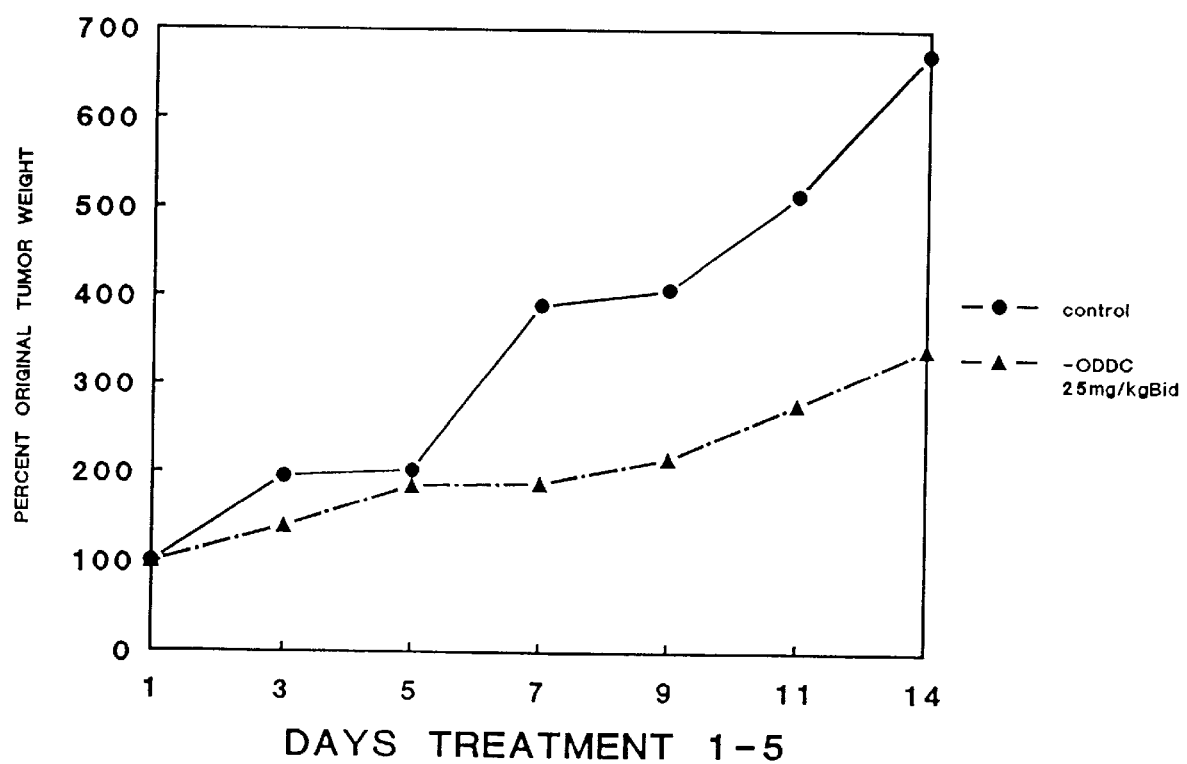
FIG. 2 is a graph of tumor growth weight for mouse carcinoma (Colon 38) treated twice a day with (−)-OddC in a dosage amount of 25 mg/kgbid. The graph plots tumor growth as a percentage of original tumor weight vs. days. Treatment of the mice occurred in days 1, 2, 3, 4 and 5. In the graph, the data for the control (no administration of (−)-OddC) is represented by (●), the data for (−)-OddC is represented by (- - ▲ - -).

Colon 38 tumor cells were implanted sc to BDF1 mice. (−)-OddC was administered to the mice twice daily for five days, at a dosage of 25 mg/kg/dose. The colon tumor cell growth was retarded as shown in FIG. 2. In FIG. 2, (●) represents the data from the control animals, and (▲) represents the data from the mice treated with (−)-OddC.

B. In Vitro Testing of (−)-OddC (−)-OddC was evaluated in the NCI's cancer screening program. The test measures the inhibition of various cancer cell lines at various concentrations of (−)-OddC. The cell lines which were tested are set forth in Table 2.

Table 2 also provides the concentration at which GI50 and TGI were observed in the tested cell lines. GI50, TGI and LC50 are values representing the concentrations at which the PG (percent of growth inhibition), defined below, is +50, 0, and −50, respectively. These values were determined by interpolation from dose response curves established for each cell line, plotted as a function of PG v. $\log_{10}$ concentration of (−)-OddC.

PG is the measured effect of (−)-OddC on a cell line and was calculated according to one of the following two expressions:
If (Mean $OD_{test}$−Mean $OD_{tzero}$)≧0. then
PG=100×(Mean $OD_{test}$−Mean $OD_{tzero}$)/(Mean $OD_{ctrl}$−Mean $OD_{tzero}$)
If (Mean $OD_{test}$−Mean $OD_{tzero}$)<0. then
PG=100×(Mean $OD_{test}$−Mean $OD_{tzero}$)/(Mean $OD_{tzero}$)
Where:
Mean $OD_{tzero}$=The average of optical density measurements of SRB-derived color just before exposure of cells to the test compound.
Mean $OD_{test}$=The average of optical density measurements of SRB-derived color after 48 hours exposure of cells to the test compound.
Mean $OD_{ctrl}$=The average of optical density measurements of SRB-derived color after 48 hours with no exposure of cells to the test compound.

In Table 2, the first two columns describe the subpanel (e.g., leukemia) and cell line (e.g., CCRF-CEM) which were treated with (−)-OddC. Column 3 indicates the $\log_{10}$ at which GI50 occurred and column 4 indicates the $\log_{10}$ at which TGI occurred. If these response parameters could not be obtained by interpolation, the value given for each response parameter is the highest concentration tested and is preceded by a ">" sign. For example, if all the PG at al concentrations of (−)-OddC given to a particular cell line exceeds +50, then this parameter can not be obtained by interpolation.

TABLE 2

| Panel | Cell Line | $\log_{10}$GI50 | $\log_{10}$TGI |
|---|---|---|---|
| Leukemia | CCRF-CEM | −6.64 | >−4.00 |
| | RL-60(TB) | −6.28 | >−4.00 |
| | K-562 | −4.59 | >−4.00 |
| | BSOLT-4 | −6.66 | −4.39 |
| | RPMI-2.26 | −4.03 | >−4.00 |
| | SR | −5.95 | >−4.00 |
| Non-Small Cell Lung Cancer | A549/ATCC | −6.01 | >−4.00 |
| | BKVX | >−4.00 | >−4.00 |
| | HOP-62 | −6.23 | −4.71 |
| | NCI-H23 | −4.92 | >−4.00 |
| | NCI-H322M | >−4.00 | >−4.00 |
| | NCI-H460 | −4.32 | >−4.00 |
| | NCI-H522 | −6.06 | >−4.00 |
| Colon Cancer | COLO205 | −4.03 | >−4.00 |
| | HCT-116 | −5.23 | >−4.00 |
| | HCT-15 | −5.39 | >−4.00 |
| | HT29 | >−4.00 | >−4.00 |
| | K2112 | >−4.00 | >−4.00 |
| CNS Cancer | SP-268 | −5.18 | >−4.00 |
| | SP-295 | −6.24 | >−4.00 |
| | SNB-19 | −5.71 | >−4.00 |
| | U251 | −4.91 | >−4.00 |
| Melanoma | LOX D6VI | −6.39 | >−4.00 |
| | MALME-3M | −4.51 | >−4.00 |
| | M14 | −6.27 | −5.07 |
| | SK-MEL-28 | −4.31 | >−4.00 |
| | SK-MEL-5 | −4.91 | >−4.00 |
| | UACC-257 | >−4.00 | >−4.00 |
| | UACC-62 | −5.53 | >−4.00 |
| Ovarian Cancer | OROV1 | −4.03 | >−4.00 |
| | OVCAR-3 | −4.44 | >−4.00 |
| | OVCAR-4 | >−4.00 | >−4.00 |
| | OVCAR-5 | −4.41 | >−4.00 |
| | OVCAR-8 | −5.82 | >−4.00 |
| | SK-OV-3 | −5.35 | >−4.00 |
| Renal Cancer | 785-4 | −5.36 | >−4.00 |
| | ACHN | −6.46 | >−4.00 |
| | CAKI-1 | −6.65 | −4.87 |
| | RXF-393 | −6.17 | >−4.00 |
| | SN12C | −6.27 | >−4.00 |
| | TK-30 | >−4.00 | >−4.00 |
| | UO-31 | −5.60 | >−4.00 |
| Prostate Cancer | PC-3 | −6.29 | >−4.00 |
| | DU-145 | −6.97 | >−4.00 |
| Breast Cancer | MCF7 | −5.95 | >−4.00 |
| | MCF7/ADR-RES | −4.97 | >−4.00 |
| | MDA-MB-231/ATCC | >−4.00 | >−4.00 |
| | HS578T | >−4.00 | >−4.00 |
| | MDA-MB-435 | −4.62 | >−4.00 |
| | MDA-N | −4.33 | >−4.00 |
| | BT-549 | −4.59 | >−4.00 |
| | T-47D | >−4.00 | >−4.00 |

Figure 4:
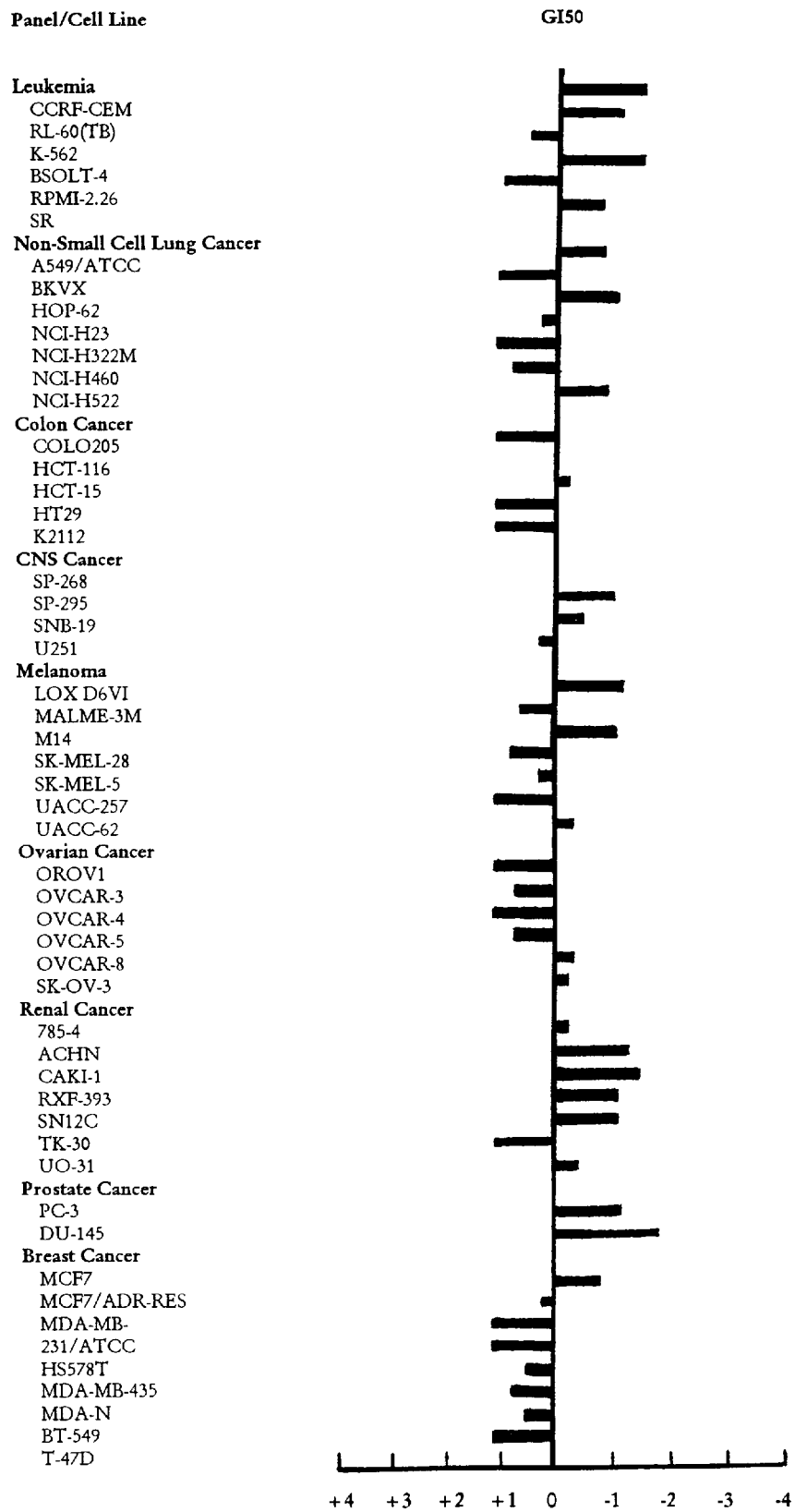
FIG. 4 is a plot of the relative sensitivity of certain cancer cell lines to (−)-OddC on the basis of GI50. Bars extending to the right represent sensitivity of the cell line to (−)-OddC in excess of the average sensitivity of all tested cell lines. Since the bar scale is logarithmic, a bar 2 units to the right implies the compound achieved GI50 for the cell line at a concentration one-hundredth the mean concentration required over all cell lines, and thus the cell line is unusually sensitive to (−)-OddC. Bars extending to the left correspondingly imply sensitivity less than the mean.

FIG. 4 is a graph that displays the relative selectivity of (−)-OddC for a particular cell line. Bars extending to the right represent sensitivity of the cell line to (−)-OddC in excess of the average sensitivity of all tested cell lines. Since the bar scale is logarithmic, a bar 2 units to the right implies the compound exhibited a GI50 for the cell line at a concentration one-hundredth the mean concentration required over all cell lines, and thus the cell line is unusually sensitive to (−)-OddC. Bars extending to the left correspondingly imply sensitivity less than the mean. These cell lines can be easily determined from Table 2, as the $\log_{10}$ concentration will be preceded by a ">".

It can be seen from FIG. 4 that at least one cell line of each type of cancer cell tested exhibited sensitivity to (−)-OddC. Certain prostate cancer cell lines, leukemia cell lines, and colon cell lines show extreme sensitivity to (−)-OddC.

IV. Use of (−)-OddC in Oligonucleotides and in Antisense Technology

Antisense technology refers in general to the modulation of gene expression through a process wherein a synthetic oligonucleotide is hybridized to a complementary nucleic acid sequence to inhibit transcription or replication (if the target sequence is DNA), inhibit translation (if the target sequence is RNA) or to inhibit processing (if the target sequence is pre-RNA). A wide variety of cellular activities can be modulated using this technique. A simple example is the inhibition of protein biosynthesis by an antisense oligonucleotide bound to mRNA. In another embodiment, a synthetic oligonucleotide is hybridized to a specific gene sequence in double stranded DNA, forming a triple stranded complex (triplex) that inhibits the expression of that gene sequence. Antisense oligonucleotides can be also used to activate gene expression indirectly by suppressing the biosynthesis of a natural repressor or directly by reducing termination of transcription. Antisense Oligonucleotide Therapy (AOT) can be used to inhibit the expression of pathogenic genes, including those which are implicated in the uncontrolled growth of benign or malignant tumor cells or which are involved in the replication of viruses, including HIV and HBV.

The stability of the oligonucleotides against nucleases is an important factor for in vivo applications. It is known that 3'-exonuclease activity is responsible for most of the unmodified antisense oligonucleotide degradation in serum. Vlassov, V. V., Yakubov, L. A., in Prospects for Antisense Nucleic Acid Therapy of Cancers and AIDS, 1991, 243–266, Wiley-Liss, Inc., N.Y.; Nucleic Acids Res., 1993, 21, 145.

The replacement of the nucleotide at the 3'-end of the oligonucleotide with (−)-OddC can stabilize the oligonucleotide against 3'-exonuclease degradation. Alternatively or in addition, an internal nucleotide can be replaced by (−)-OddC to resist the degradation of the oligonucleotide by endonucleases.

Given the disclosure herein, one of ordinary skill in the art will be able to use (−)-OddC to stabilize a wide range of oligonucleotides against degradation by both exonucleases and endonucleases, including nucleosides used in antisense oligonucleotide therapy. All of these embodiments are considered to fall within the scope of this invention. Example 11 provides one, non-limiting, example of the use of (−)-OddC to resist the activity of a 3'-exonuclease.

EXAMPLE 11

Resistance to 3'-Exonuclease Activity By (−)-OddC

The human cytosolic exonuclease activity from human H9 (T-type lymphocytic leukemic cells) was determined by sequencing gel assay. Briefly, the 3'-terminated substrate was prepared from a 20 or 23 base-long DNA primer with the following sequence:

3'-CAATTTTGAATTTCCTTAACTGCC-5'
24                                                 1

The primers were labelled at the 5'-end with [Y-$^{32}$P]ATP, annealed to complementary RNA templates and terminated at the 3' end with dTTP (20 mer) dCTP (23 mer) or L-OddCTP (23 mer) in a standing start reaction catalyzed by HIV-1 RT. Under these conditions, the 20 mer was terminated with dTMP (A) the 23 mer was terminated with dCMP (B) or L-OddCMP(C). These single stranded DNA substrates were used to assay their susceptibility to the cytoplasmic exonuclease. The assays were done in 10 µl reactions containing 50 mM Tris-HCl pH 8.0, 1 mM $MgCl_2$, 1 mM dithiothreitol, 0.1 mg/ml bovine serum albumin, 0.18 µCi/ml 3'-terminated substrate and 2 µl of the exonuclease (0.03 units). The reactions were incubated at 37° C. for the indicated times and terminated by adding 4 µl 98% formamide, 10 mM EDTA and 0.025% bromophenol blue. The samples were denatured at 100° C. for 5 minutes followed by rapid cooling on ice. The unreacted material as well as the reaction products were separated on 15% polyacrylamide/urea sequencing gels and visualized by autoradiography. The oligonucleotide with (−)-OddC at the 3'-end was at least five times more resistant to 3'-exonuclease than the other oligonucleotides.

Modifications and variations of the present invention in the treatment of cancer will be obvious to those skilled in the art from the foregoing detailed description of the invention. Such modifications and variations are intended to come within the scope of the appended claims.

---

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
        ( A ) LENGTH: 24 base pairs
        ( B ) TYPE: nucleic acid
        ( C ) STRANDEDNESS: single
        ( D ) TOPOLOGY: linear ( i i ) MOLECULE TYPE: Other nucleic acid ( i i i ) HYPOTHETICAL: NO ( i v ) ANTI-SENSE: NO -continued ( x i ) SEQUENCE DESCRIPTION: SEQ ID NO:1:

CAATTTGAA TTTCCTTAAC TGCC                                                                                    2 4

We claim:

1. A method for treating tumors comprising administering to a host animal an effective amount of a compound of the formula

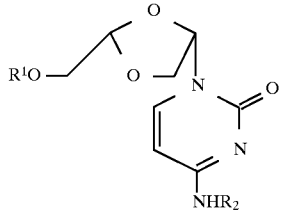

wherein $R^1$ and $R^2$ are independently selected from the group consisting of hydrogen, $C_1$ to $C_{18}$ alkyl, and an acyl group in which the non-carbonyl moiety of the ester group is selected from straight, branched, or cyclic $C_1$ to $C_{18}$ alkyl, methoxymethyl, phenoxymethyl, phenyl, sulfonate ester, and mono, di and triphosphate ester said tumors being sensitive to treatment with said compound.

2. The method of claim 1, wherein the host animal is a human.

3. The method of claim 1, wherein the tumor is cancerous and the cancer is prostate cancer.

4. The method of claim 1, wherein the tumor is cancerous and the cancer is leukemia.

5. The method of claim 1, wherein the tumor is cancerous and the cancer is colon cancer.

6. The method of claim 1, wherein the tumor is lung cancer.

7. The method of claim 1, wherein the tumor is hepatoma.

8. The method of claim 1, wherein $R^1$ and $R^2$ are selected from the group consisting of hydrogen and an acyl group.

9. A method for treating tumors sensitive to treatment with (−)-(2S,4S)-1-(2-hydroxymethyl-1,3-dioxolane-4-yl) cytosine comprising administering to a host animal an effective amount of (−)-(2S,4S)-1-(2-hydroxymethyl-1,3-dioxolane-4-yl)cytosine.

10. The method of claim 9, wherein the tumor is cancerous.

11. The method of claim 10, wherein the host animal is a human.

12. The method of claim 9, wherein the tumor is cancerous and the cancer is prostate.

13. The method of claim 9, wherein the cancer is leukemia.

14. The method of claim 9, wherein the cancer is colon cancer.

15. The method of claim 9, wherein the tumor is lung cancer.

16. The method of claim 9, wherein the tumor is hepatoma.

17. A method for treating cancer comprising administering to a host animal an effective amount of a compound of the formula:

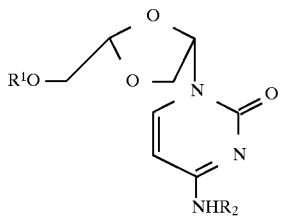

wherein $R^1$ and $R^2$ are independently selected from the group consisting of hydrogen, $C_1$ to $C_{18}$ alkyl, and an acyl group in which the non-carbonyl moiety of the ester group is selected from straight, branched, or cyclic $C_1$ to $C_{18}$ alkyl, methoxymethyl, phenoxymethyl, phenyl, sulfonate ester, and mono, di and triphosphate ester, said cancer being sensitive to treatment with said compound.

18. The method of claim 17, wherein the host animal is a human.

19. The method of claim 17, wherein $R^1$ and $R^2$ are selected from the group consisting of hydrogen and an acyl group.

* * * * *

UNITED STATES PATENT AND TRADEMARK OFFICE
CERTIFICATE OF CORRECTION

PATENT NO. : 5,817,667
DATED : 9/6/94
INVENTOR(S) : Yung-Chi Cheng, C.K. Chu

It is certified that error appears in the above-identified patent and that said Letters Patent is hereby corrected as shown below:

Column 1, after the title insert the following:

The invention identified above is a subject invention under 35 U.S.C. 200, et seq., and the Standard Patent Rights Clause at 37 C.F.R. 401.14 or F.A.R. 52.227-11, which are included among the terms of the above-identified grant/contract award from the Public Health Service/National Institutes of Health.

Signed and Sealed this

Thirteenth Day of April, 1999

*Attest:*

Q. TODD DICKINSON

*Attesting Officer*  *Acting Commissioner of Patents and Trademarks*